United States Patent
Tanaka et al.

(10) Patent No.: US 8,184,146 B2
(45) Date of Patent: May 22, 2012

(54) MEDICAL IMAGE PROCESSING APPARATUS AND MEDICAL IMAGE PROCESSING METHOD

(75) Inventors: Hideki Tanaka, Tama (JP); Hirokazu Nishimura, Hachioji (JP); Kenji Nakamura, Chiba (JP); Ryoko Inoue, Hachioji (JP); Miho Sawa, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 923 days.

(21) Appl. No.: 12/208,827

(22) Filed: Sep. 11, 2008

(65) Prior Publication Data
US 2009/0073257 A1  Mar. 19, 2009

Related U.S. Application Data

(63) Continuation of application No. PCT/JP2007/053585, filed on Feb. 27, 2007.

(30) Foreign Application Priority Data

Mar. 14, 2006 (JP) .................................. 2006-069816

(51) Int. Cl.
*H04N 13/00* (2006.01)
(52) U.S. Cl. ................ 348/45; 348/43; 348/46; 348/47; 348/65; 348/68
(58) Field of Classification Search .................... 348/43, 348/45, 65, 68, 46, 47
See application file for complete search history.

(56) References Cited

U.S. PATENT DOCUMENTS

| 5,611,025 A | 3/1997 | Lorensen et al. |
| 5,751,341 A * | 5/1998 | Chaleki et al. .................. 348/65 |
| 6,515,657 B1 * | 2/2003 | Zanelli .......................... 345/419 |
| 6,556,695 B1 * | 4/2003 | Summers et al. ............. 382/128 |
| 6,909,802 B2 * | 6/2005 | Nakamura .................... 382/154 |
| 7,150,716 B2 * | 12/2006 | Jones et al. ................... 600/446 |
| 7,260,250 B2 * | 8/2007 | Summers et al. ............. 382/128 |

FOREIGN PATENT DOCUMENTS

| JP | 08-252217 | 10/1996 |
| JP | 08-256295 | 10/1996 |

OTHER PUBLICATIONS

Oda et al, "Reconstruction of the Gastric Surface Structure Using a Monocular CCD Endoscope", Optical Review, vol. 2, No. 2, 1995, pp. 110-114.*

Oda et al., "Reconstruction of the Gastric Surface Structure Using a Monocular CCD Endoscope", Optical Review, vol. 2, No. 2, 1995, pp. 110-114.

Chinese Office Action dated Feb. 5, 2010.

* cited by examiner

*Primary Examiner* — Liangche A Wang
(74) *Attorney, Agent, or Firm* — Scully, Scott, Murphy & Presser, P.C.

(57) ABSTRACT

An image processing apparatus includes: a surface model generation section for performing processing for generating a three-dimensional surface model from a two-dimensional medical image; and an area reliability calculation section for dividing the surface model into multiple areas and calculating the reliability of data in each of the multiple areas.

14 Claims, 12 Drawing Sheets

MEDICAL IMAGE PROCESSING APPARATUS AND MEDICAL IMAGE PROCESSING METHOD

CROSS REFERENCE TO RELATED APPLICATION

This application is a continuation application of PCT/JP2007/053585 filed on Feb. 27, 2007 and claims benefit of Japanese Application No. 2006-069816 filed in Japan on Mar. 14, 2006, the contents of which are incorporated herein by this reference.

BACKGROUND OF INVENTION

1. Field of the Invention

The present invention relates to a medical image processing apparatus and a medical image processing method for processing the reliability of each portion in a three-dimensional surface model generated from a two-dimensional image.

2. Description of the Related Art

An endoscopic image obtained by an endoscope inserted in a body cavity is widely used for diagnosis of an observed region. The endoscopic image obtained by the endoscope is a two-dimensional image. Therefore, there is an apparatus for creating a three-dimensional surface model from the obtained image information and displaying the created surface model to provide image information from which diagnosis can be made more easily, for example, like a conventional example disclosed in Japanese Patent Application Laid-Open Publication No. 08-252217.

When a three-dimensional surface model is created and displayed as described above, the image makes it easier to make a diagnosis in comparison with a two-dimensional endoscopic image.

In the case of the inside of a body cavity, especially in the case of a lumen shape, when there are folds or protrusions in the lumen portion, the positions behind the folds or the projections cannot be seen from the position to be an observation point (that is, the observation window).

SUMMARY OF THE INVENTION

A medical image processing apparatus according to the present invention includes: a surface model generation section for performing processing for generating a three-dimensional surface model from a two-dimensional medical image; and an area reliability calculation section for dividing the surface model into multiple areas and calculating the reliability of data in each of the multiple areas.

Furthermore, a medical image processing method according to the present invention includes: a surface model generation step of performing processing for generating a three-dimensional surface model from a two-dimensional medical image; and an area reliability calculation step of dividing the surface model into multiple areas and calculating the reliability of data in each of the multiple areas.

BRIEF DESCRIPTION OF THE DRAWINGS

FIG. 7 is a diagram showing positional relationship between a corresponding point on a body which corresponds to each pixel of a picked-up image and a light source and the like;

DETAILED DESCRIPTION OF THE PREFERRED EMBODIMENT(S)

Figure 1:
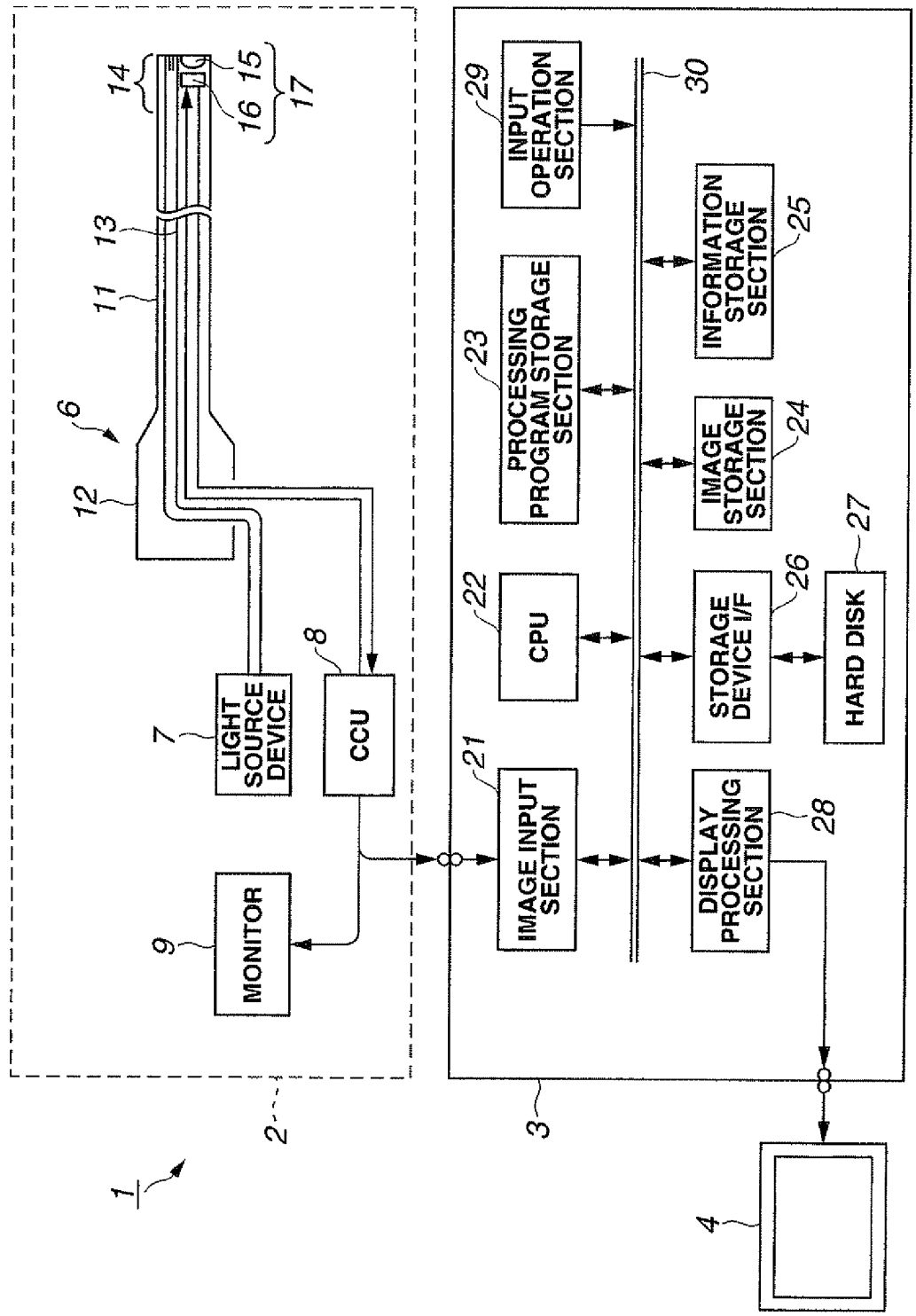
FIG. 1 is a block diagram showing the configuration of an endoscope system.
Figure 2:
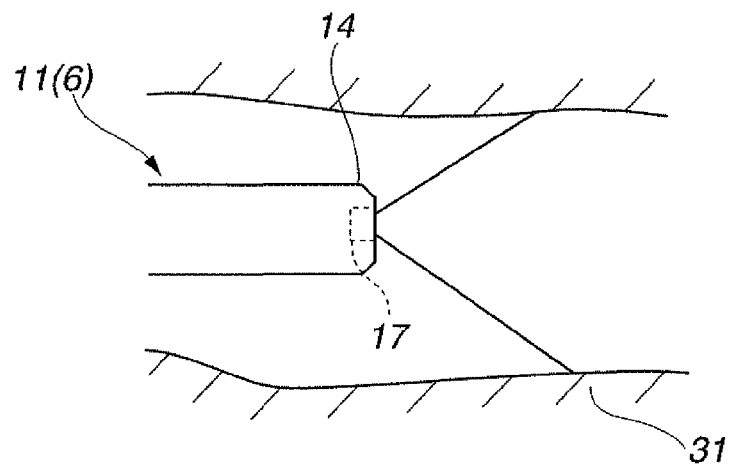
FIG. 2 is a diagram showing that an image is picked up by an endoscope inserted in a tubular region such as a large intestine.
Figure 3:
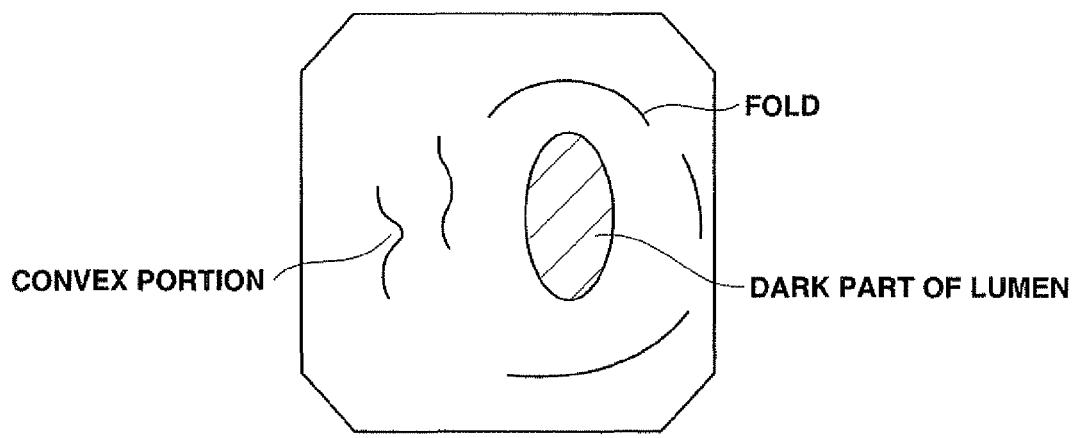
FIG. 3 is a diagram showing an endoscopic image picked up by an image pickup apparatus provided on the endoscope in FIG. 2.
Figure 4:
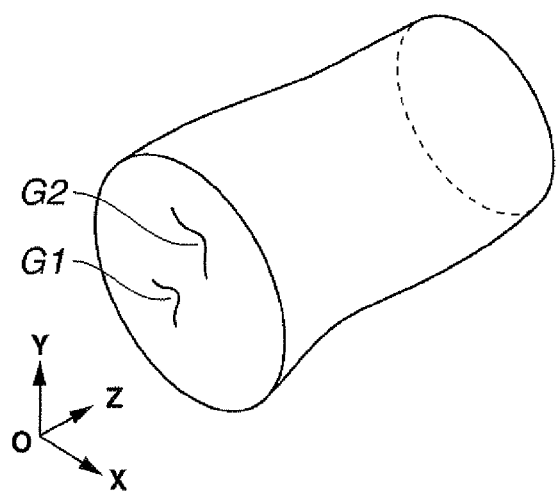
FIG. 4 is a diagram showing a surface model generated from the endoscopic image in FIG. 3.
Figure 5:
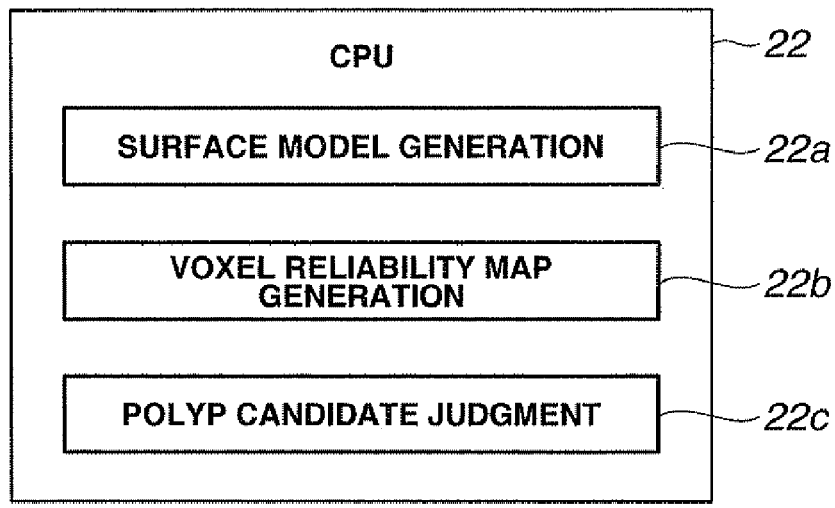
FIG. 5 is a block diagram showing an image analysis processing function by a CPU.
Figure 6:
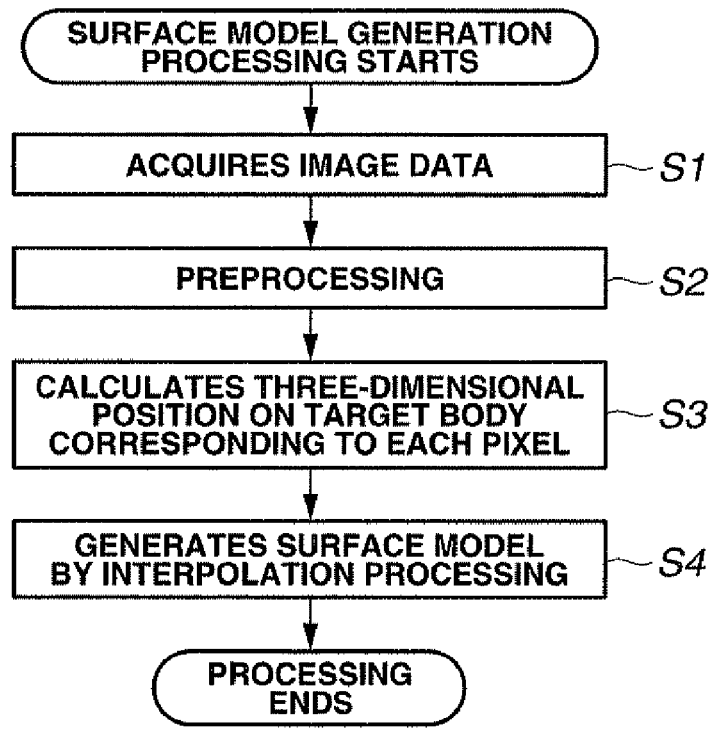
FIG. 6 is a flowchart showing a procedure for generating a surface model.
Figure 7:
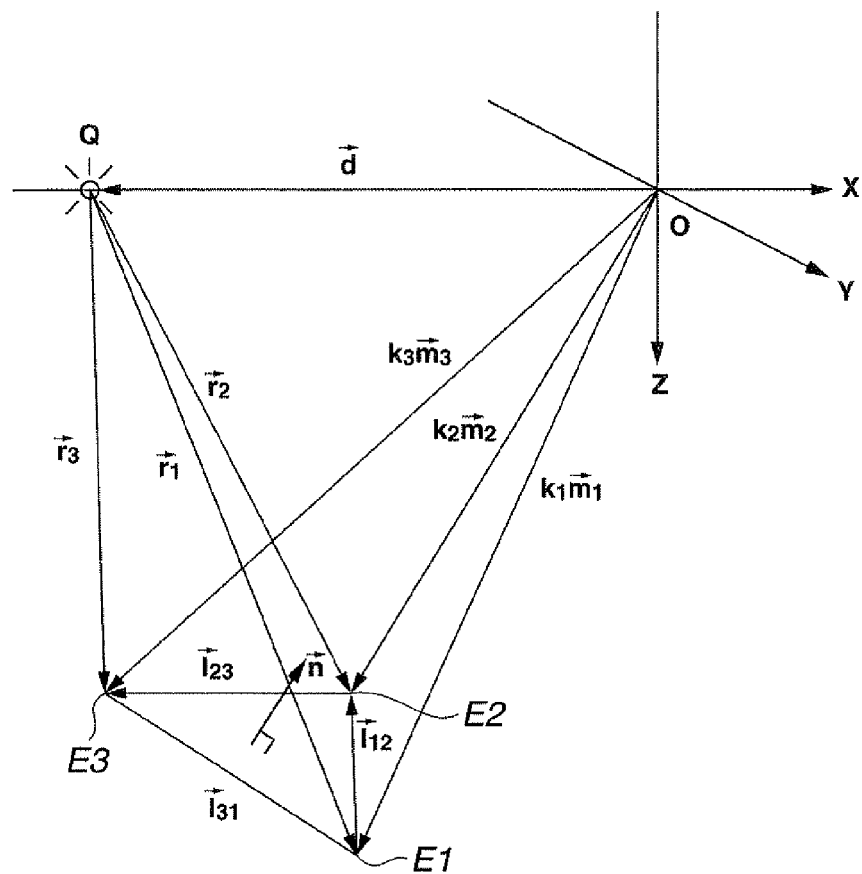
Figure 8A:
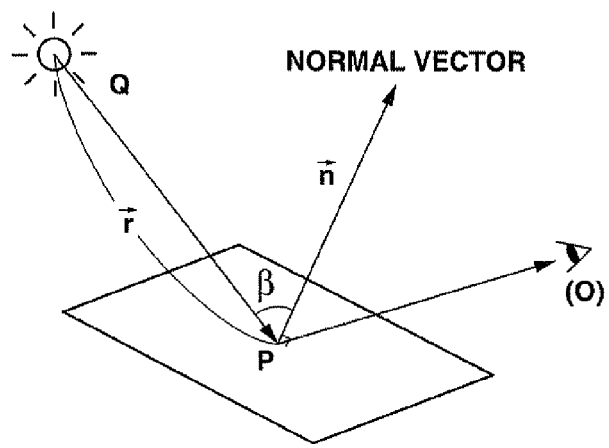
FIG. 8A is a diagram showing that a light from a light source is reflected by the surface of a body.
Figure 8B:
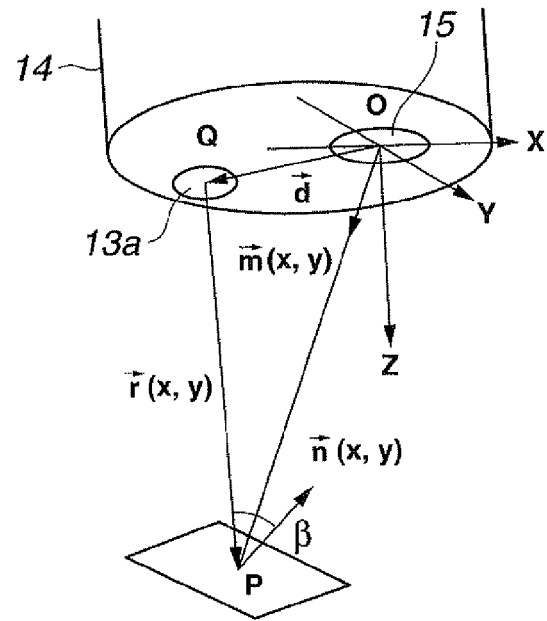
FIG. 8B is a diagram showing that a light from a light source is reflected by the surface of a body.
Figure 9:
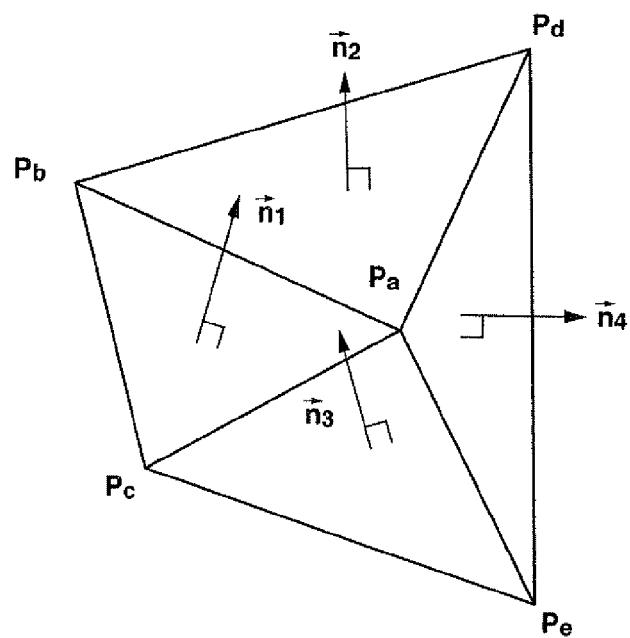
FIG. 9 is a diagram showing multiple normal vectors set around a corresponding point.
Figure 10:
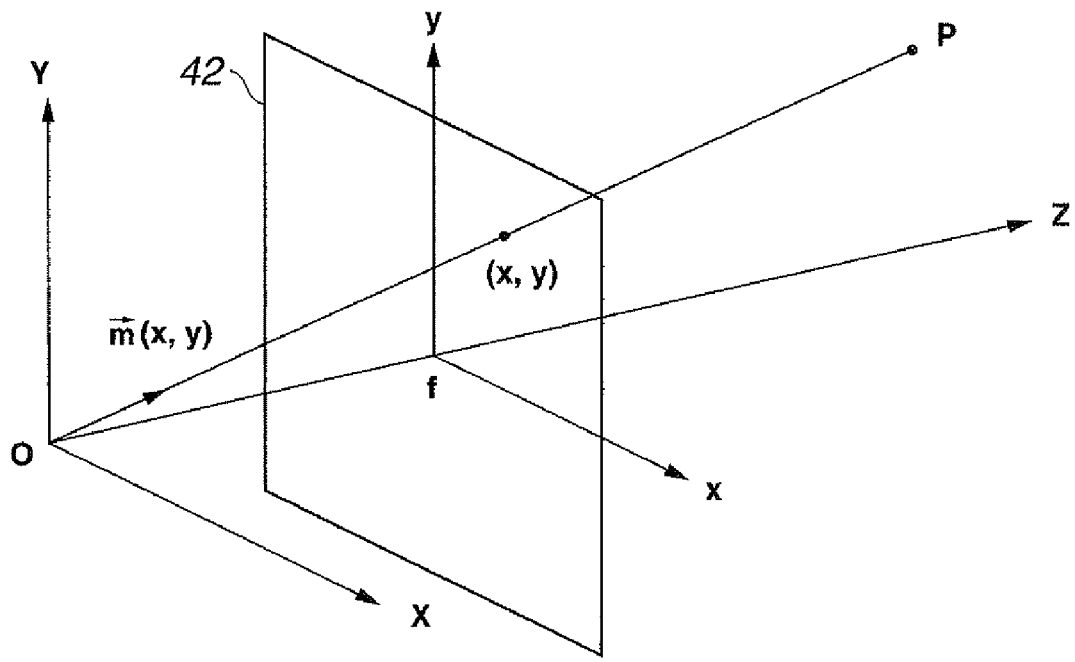
FIG. 10 is a diagram showing that a vector m in FIG. 8B passes through a position on a two-dimensional image.
Figure 11:
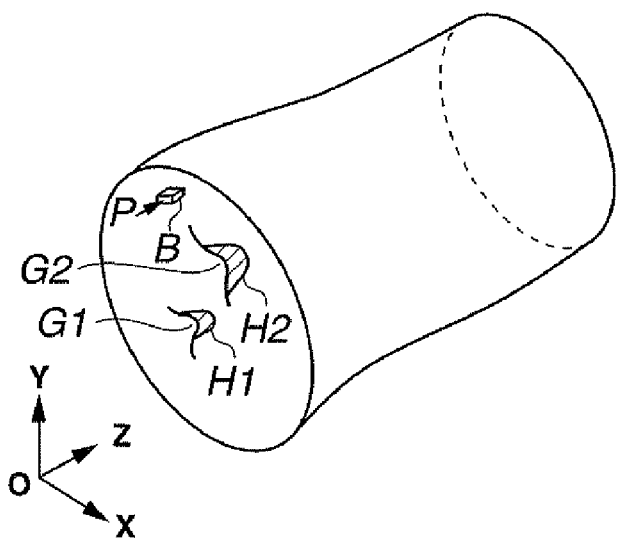
FIG. 11 is a diagram showing a surface model generated at step S2 in FIG. 6.
Figure 12:
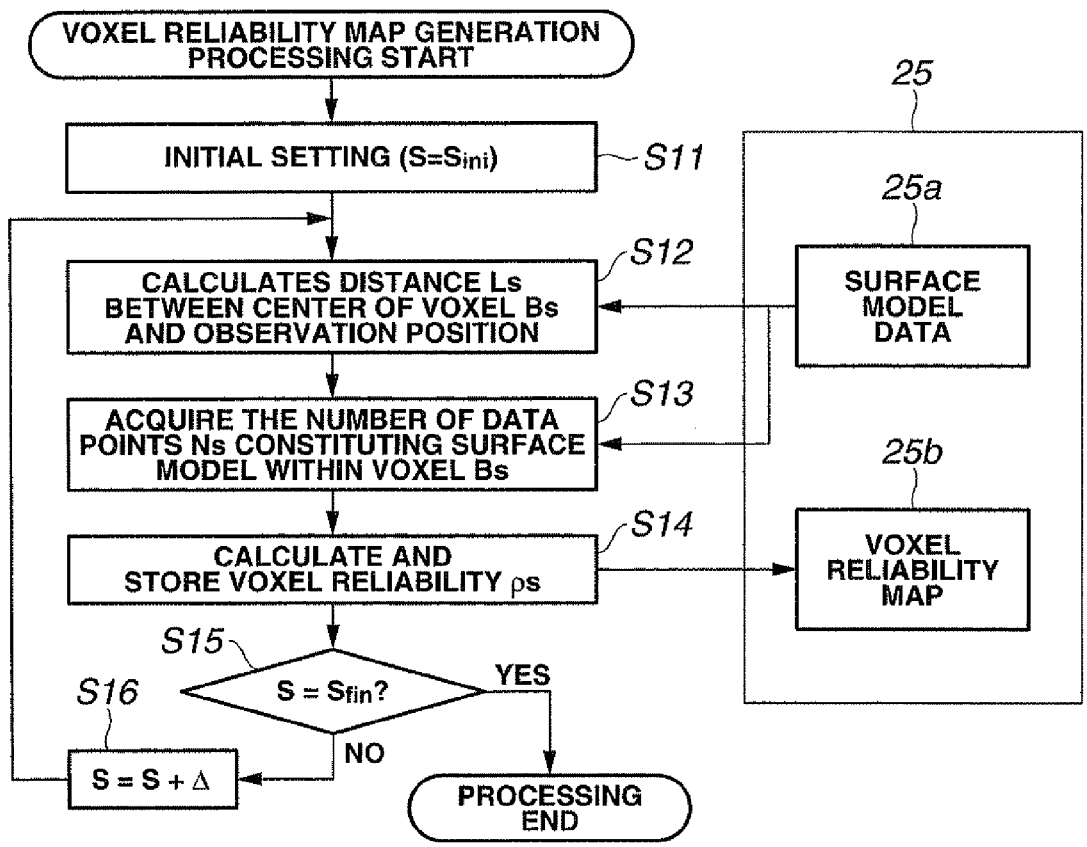
FIG. 12 is a diagram showing the contents of processing for generating a voxel reliability map, and data and the like to be used.
Figure 13:
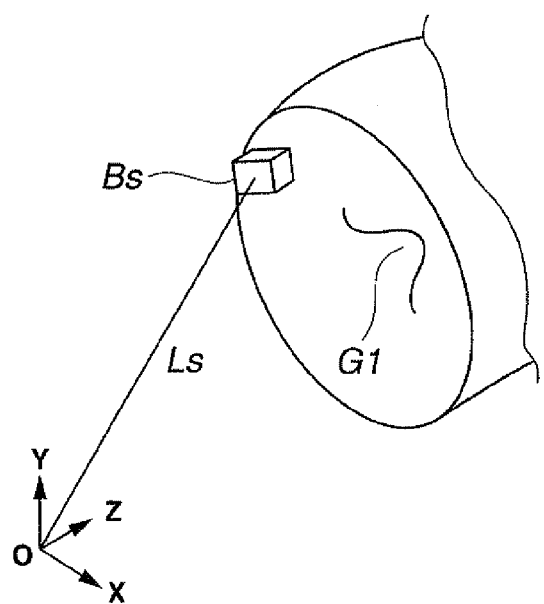
FIG. 13 is a diagram for illustrating distance calculation by step S12 in FIG. 12.
Figure 14:
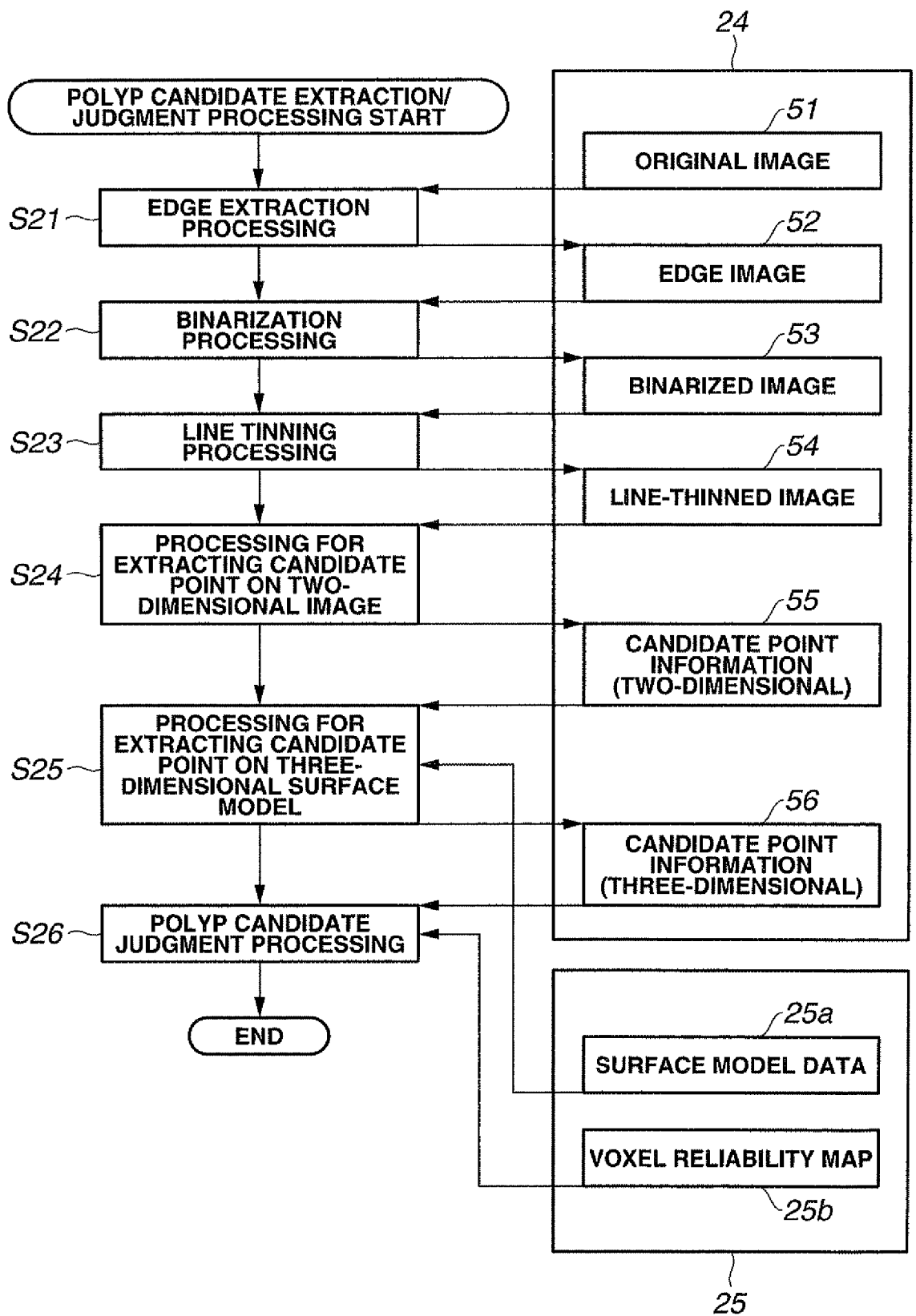
FIG. 14 is a diagram showing the contents of processing for performing polyp candidate extraction and judgment, and images and the like to be generated/used.
Figure 15A:
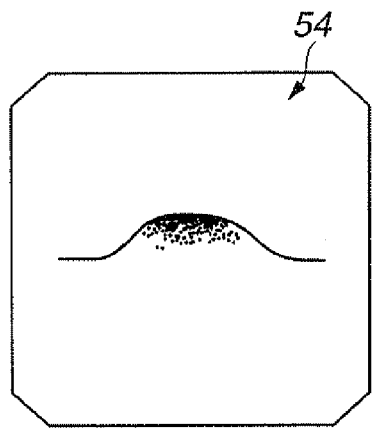
FIG. 15A is a diagram for illustrating the operation of step S24 in FIG. 14.
Figure 15B:
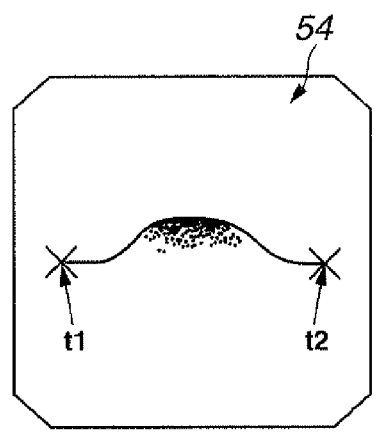
FIG. 15B is a diagram for illustrating the operation of step S24 in FIG. 14.
Figure 15C:
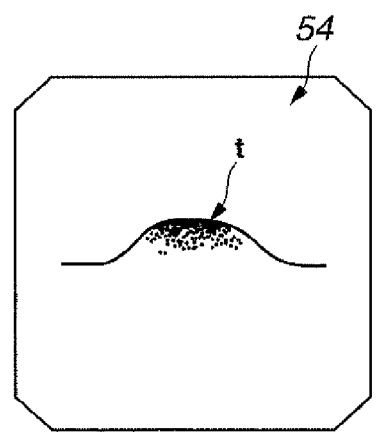
FIG. 15C is a diagram for illustrating the operation of step S24 in FIG. 14.
Figure 15D:
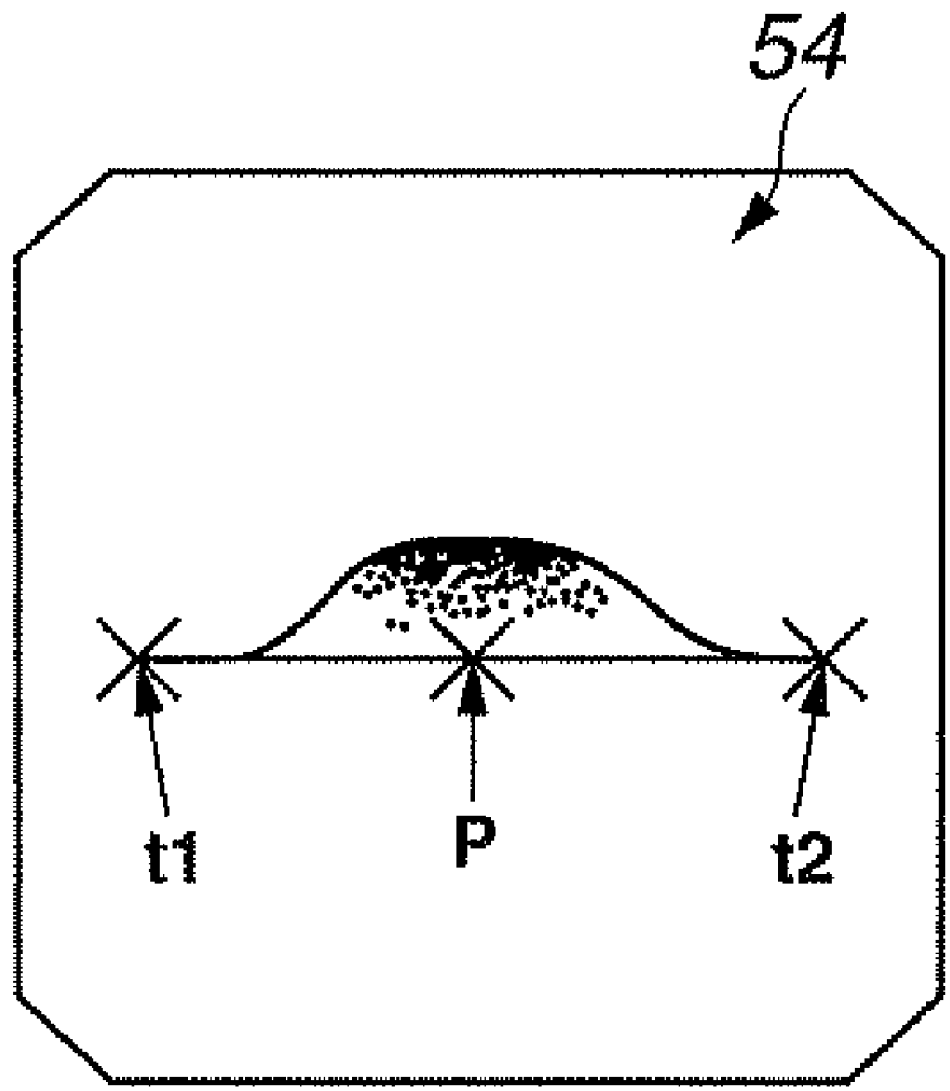
FIG. 15D is a diagram for illustrating the operation of step S24 in FIG. 14.
Figure 16:
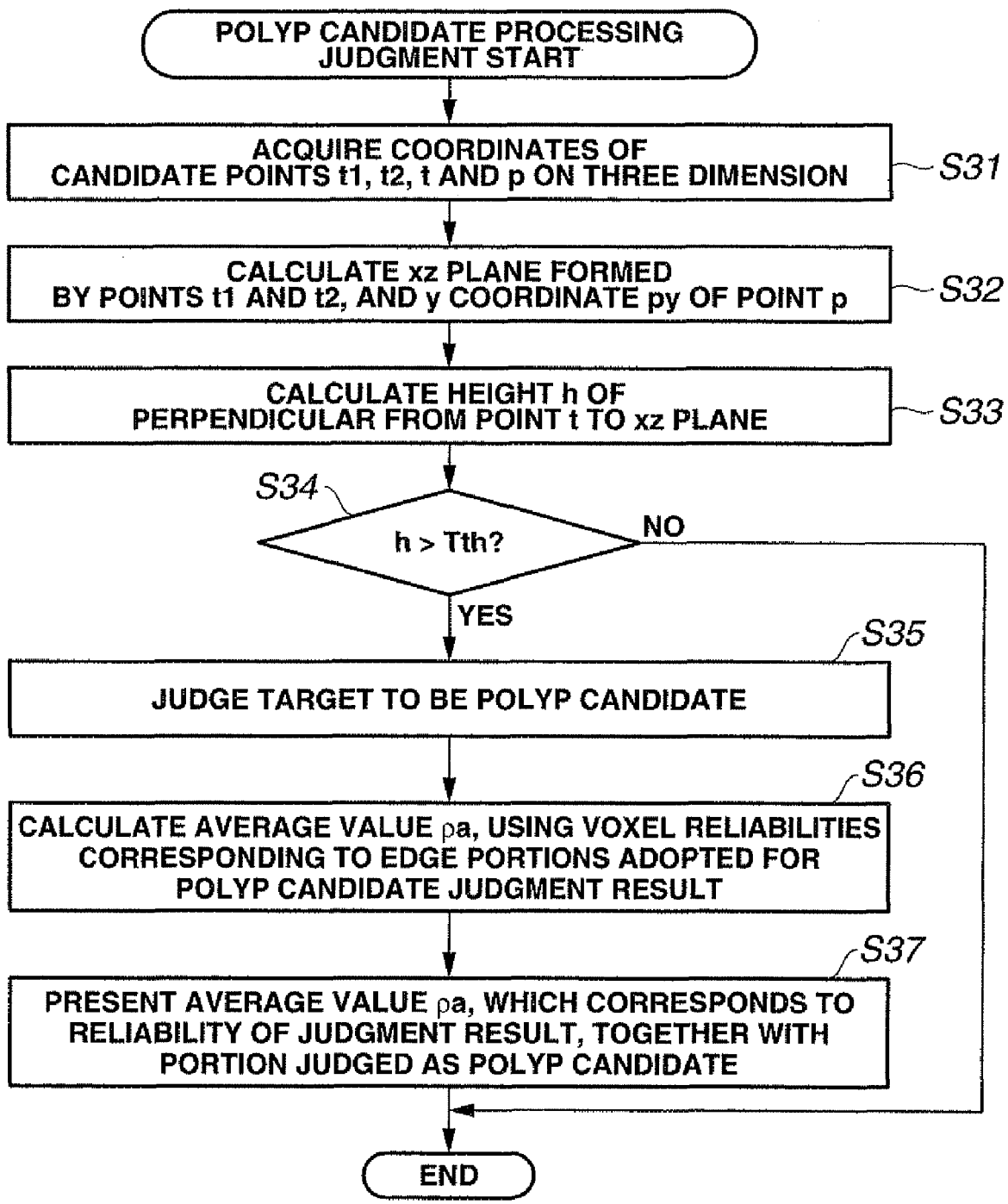
FIG. 16 is a flowchart showing the contents of polyp candidate judgment processing of step S26 in FIG. 14.
Figure 17:
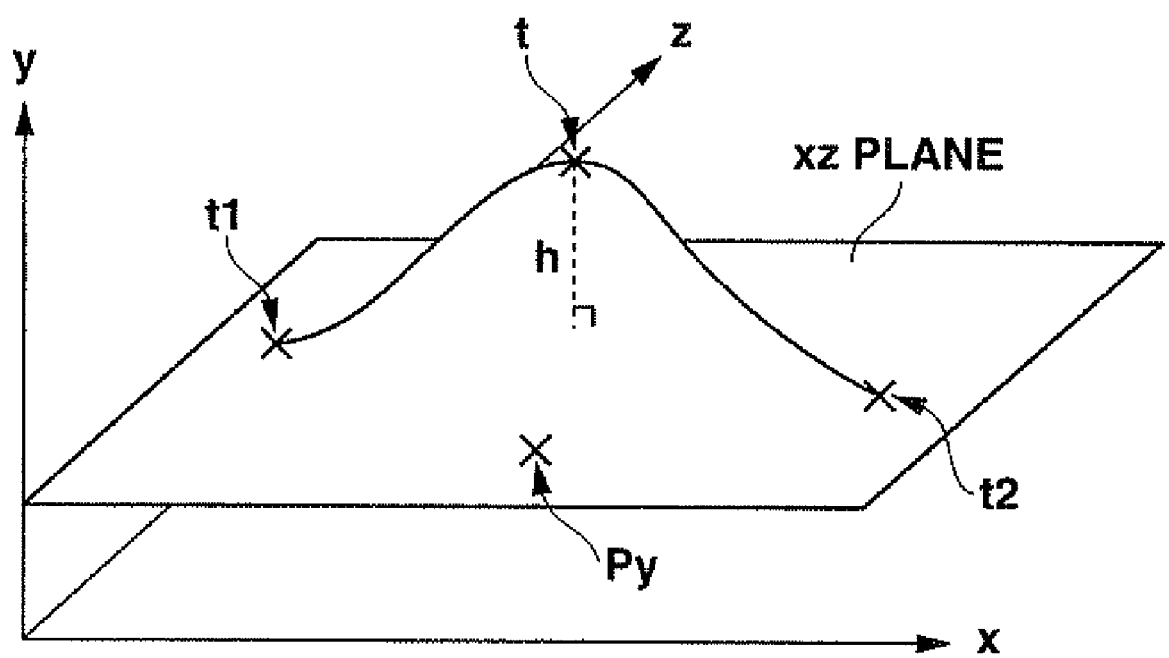
FIG. 17 is a diagram for illustrating the processing in FIG. 16.

An embodiment of the present invention will be described below with reference to drawings. FIGS. 1 to 17 are related to an embodiment of the present invention. FIG. 1 is a block diagram showing the configuration of an endoscope system; FIG. 2 is a diagram showing that an image is picked up by an endoscope inserted in a tubular region such as a large intestine; FIG. 3 is a diagram showing an endoscopic image picked up by an image pickup apparatus provided on the endoscope in FIG. 2; FIG. 4 is a diagram showing a surface model generated from the endoscopic image in FIG. 3; FIG. 5 is a block diagram showing an image analysis processing function by a CPU; FIG. 6 is a flowchart showing a procedure for generating a surface model; FIG. 7 is a diagram showing positional relationship between a corresponding point on a body which corresponds to each pixel of a picked-up image and a light source or the like; FIG. 8A is a diagram showing that a light from a light source is reflected by the surface of a body; FIG. 8B is a diagram showing that a light from a light source is reflected by the surface of a body; FIG. 9 is a diagram showing multiple normal vectors set around a corresponding point; FIG. 10 is a diagram showing that a vector m in FIG. 8B passes through a position on a two-dimensional image; FIG. 11 is a diagram showing a surface model generated at step S2 in Fig in FIG. 6; FIG. 12 is a diagram showing the contents of processing for generating a voxel reliability map, and data and the like to be used; FIG. 13 is a diagram for illustrating distance calculation by step S12 in FIG. 12; FIG. 14 is a diagram showing the contents of processing for performing polyp candidate extraction and judgment, and images and the like to be generated/used; FIG. 15A is a diagram for illustrating the operation of step S24 in FIG. 14; FIG. 15B is a diagram for illustrating the operation of step S24 in FIG. 14; FIG. 15C is a diagram for illustrating the operation of step S24 in FIG. 14; FIG. 15D is a diagram for illustrating the operation of step S24 in FIG. 14; FIG. 16 is a flowchart showing the contents of polyp candidate judgment processing of step S26 in FIG. 14; and FIG. 17 is a diagram for illustrating the processing in FIG. 16.

An endoscope system 1 shown in FIG. 1 is configured by an endoscope observation apparatus 2, a medical image processing apparatus (hereinafter shortened simply as an image processing apparatus) 3, which is configured by a personal computer or the like, for performing image processing of an endoscopic image as a medical image obtained by the endoscope observation apparatus 2, and a display monitor 4 for displaying an image for which image processing has been performed by the image processing apparatus 3.

The endoscope observation apparatus 2 has an endoscope 6 to be inserted into a body cavity, a light source device 7 which supplies illumination light to the endoscope 6, a camera control unit (abbreviated as a CCU) 8 which performs signal processing for image pickup means of the endoscope 6, and a monitor 9 which displays an endoscopic image picked up by an image pickup device by a video signal outputted from the CCU 8 being inputted.

The endoscope 6 has an insertion section 11 to be inserted into a body cavity, and an operation section 12 provided at the rear end of the insertion section 11. A light guide 13 which transmits illumination light is inserted through the insertion section 11.

The rear end of the light guide 13 is connected with the light source device 7. Illumination light supplied from the light source device 7 is transferred by the light guide 13, and (the transmitted illumination light) is emitted from a distal end surface attached to an illumination window provided on a distal end portion 14 of the insertion section 11 to illuminate a subject such as a diseased portion.

There is provided an image pickup apparatus 17 configured by an objective lens 15 attached to an observation window adjacent to the illumination window and, for example, a charge coupled device (abbreviated as a CCD) 16 as a solid-state image-pickup device which is arranged at the image formation position of the objective lens 15. An optical image formed on the image pickup surface of the CCD 16 is photoelectrically converted by the CCD 16.

The CCD 16 is connected to the CCU 8 via a signal line. By a CCD driving signal being applied from the CCU 8, the CCD 16 outputs a photoelectrically converted image signal. Signal processing is performed for the image signal by a video processing circuit within the CCU 8, and the image signal is converted to a video signal. The video signal is outputted to the monitor 9, and an endoscopic image is displayed on the display surface of the monitor 9. The video signal is also inputted to the image processing apparatus 3.

The image processing apparatus 3 has an image input section 21 to which a video signal corresponding to an endoscopic image inputted from the endoscope observation apparatus 2 is inputted, a CPU 22 as a central processing unit which performs image processing of image data inputted from the image input section 21, and a processing program storage section 23 which stores a processing program (control program) for causing the CPU 22 to perform image processing.

Furthermore, the image processing apparatus 3 has an image storage section 24 which stores image data and the like inputted from the image input section 21, an information storage section 25 which stores information and the like processed by the CPU 22, a hard disk 27 as a storage device which stores image data, information and the like processed by the CPU 22, via a storage device interface 26, a display processing section 28 which performs display processing for displaying image data and the like processed by the CPU 22, and an input operation section 29 configured by a keyboard and the like for a user to input image processing parameters and the like or perform instruction operations.

A video signal generated by the display processing section 28 is displayed on the display monitor 4. On the display surface of the display monitor 4, a processed image which has been image-processed is displayed. The image input section 21, the CPU 22, the processing program storage section 23, the image storage section 24, the information storage section 25, the storage device interface 26, the display processing section 28 and the input operation section 29 are connected with one another via a data bus 30.

In the present embodiment, the insertion section 11 of the direct-view endoscope 6 is inserted into a tubular region (tubular organ), for example, like a large intestine 31, and an image is picked up by the image pickup apparatus 17, as shown in FIG. 2.

FIG. 3 shows an example of an endoscopic image picked up by the direct-view endoscope 6. In the endoscopic image, folds and convex portions exist. The portion with oblique lines indicates a dark part of the lumen extending toward the deep part.

In the present embodiment, an image of a tubular organ such as the large intestine 31 is picked up by the endoscope 6 of a direct-view type or the like, and, from the picked-up two-dimensional endoscopic image, a three-dimensional shaped surface model of a target body (specifically, the internal surface of the luminal shape of a large intestine) is estimated. For example, FIG. 4 shows an example of the estimated surface model. In FIG. 4, convex portions G1 and G2 corresponding to the convex portions in FIG. 3 are generated.

In the case of generating a surface model as a three-dimensional shape as shown in FIG. 4, from the image data of the two-dimensional endoscope image in FIG. 3, since the illumination intensity is low at a portion at a long distance from the position of the illumination window at the distal end surface of the endoscope 6, in comparison with a portion at a short distance, the accuracy of three-dimensional data in the surface model, which is generated to correspond to the portion, deteriorates.

If there are folds or convex portions in a lumen, the positions behind the folds or the convex portions cannot be seen from the observation window at the observation position. Therefore, the accuracy of the three-dimensional data of the surface model which is generated on the basis of estimation deteriorates.

In the present embodiment, in consideration of these points, a reliability map is generated which indicates the reliability of the data of a surface or a position of each point (a voxel as a small area, as described later) in a generated three-dimensional surface model.

Then, information about the reliability of the data in each part of the generated three-dimensional surface model can be effectively used for detection, judgment or the like of a lesion.

For this purpose, the CPU 22 constituting the image processing apparatus in the present embodiment has an image processing function as shown in FIG. 5.

The CPU 22 has a surface model generation function 22a as surface model generation means for performing processing for generating (estimating) a surface model as a three-dimensional shape from a two-dimensional endoscopic image, a voxel reliability map generation function 22b as area reliability calculation means for generating a voxel reliability map which indicates, for a voxel as a small area in each part of the surface data of the generated surface model, the reliability of the data in the voxel portion, and a polyp candidate judgment function (polyp candidate detection function) 22c as candidate detection means for extracting a lesion candidate, concretely a polyp candidate, from the surface data of the surface model and performing judgment processing (or detection processing) for judging (detecting) the possibility of a polyp.

In the present embodiment, as described above, a three-dimensional surface model is generated; each part of the surface data of the surface model is regarded as an aggregate of voxels; and the reliability of the three-dimensional data in each voxel portion (voxel reliability) is calculated.

Then, for example, in the case of performing image processing for detecting or judging a lesion such as a polyp, from a generated three-dimensional surface model, more reliable detection or judgment can be performed by utilizing the reliability information.

Since the reliability information is presented together with a presented result of detection or judgment of a lesion such as a polyp, an operator can utilize the result more effectively when diagnosing a polyp and the like and can make a more appropriate diagnosis.

In the present embodiment, each of the functions shown in FIG. 5 is realized as software. That is, the CPU 22 reads the processing program stored in the processing program storage section 23. Then, by performing processing in accordance with the processing program, the CPU 22 executes the processing of the flowchart corresponding to the surface model generation function 22a shown in FIG. 6, and the like.

Next, the operation of the present embodiment will be described.

When the operation of the image processing apparatus 3 starts, the CPU 22 reads the processing program in the processing program storage section 23 and starts processing in accordance with the processing program. As shown in FIG. 6, at a first step S1, the CPU 22 acquires an endoscopic image inputted from the CCU 8 of the endoscope observation apparatus 2 via the image input section 21 as the image data of an original image.

Then, at next step S2, the CPU 22 performs preprocessing such as distortion aberration correction (for example, distortion aberration correction described in Japanese Patent Application Laid-Open Publication No. 08-256295) and noise removal, for the acquired image data. At step S3, the CPU 22 determines the three-dimensional position of a target body corresponding to a pixel in the image.

As shown in FIG. 7, points-corresponding-to-pixels E1, E2 and E3 on the target body corresponding to three pixels of an image picked up by the image pickup means existing at an observation point O are extracted. A following formula (1) can be determined from the positional relationship between the three-dimensional positions of the points-corresponding-to-pixels E1, E2 and E3 and a light source Q and the observation point O:

[Formula 1]

$$\vec{r}_1 = \vec{d} - k_1 \vec{m}_1$$

$$\vec{r}_2 = \vec{d} - k_2 \vec{m}_2$$

$$\vec{r}_3 = \vec{d} - k_3 \vec{m}_3 \quad (1)$$

Here, k1*m*1, k2*m*2 and k3*m*3 (m1, m2 and m3: unit vector the size of which is 1) denote the vectors at the three-dimensional positions of the points-corresponding-to-pixels E1, E2 and E3; d denotes the vector from the observation point O to the light source Q; and r1, r2 and r3 denote the vectors from the light source Q to the three-dimensional positions of the three points-corresponding-to-pixels E1, E2 and E3.

When n denotes a normal vector of a plane determined by the three-dimensional positions of the points-corresponding-to-pixels E1, E2 and E3, the vector n is expressed by a following formula (2), on the basis of the formula (1), and it is expressed by the ratio of vector components k1, k2 and k3.

[Formula 2]

$$\vec{n}_1 = \vec{l}_{12} \times \vec{l}_{23} = k_1 k_2 k_3 \left( \frac{1}{k_3} \vec{m}_1 \times \vec{m}_2 + \frac{1}{k_1} \vec{m}_2 \times \vec{m}_3 + \frac{1}{k_2} \vec{m}_3 \times \vec{m}_1 \right). \quad (2)$$

Here, l12 denotes the vector from the point E1 to the point E2; l23 denotes the vector from the point E2 to the point E3; and x denotes the outer product. If it is assumed that the surface of the target body (such as the internal surface of a large intestine) to be targeted by image pickup has such a diffuse reflectance that light is uniformly reflected in all directions as shown in FIG. 5A, luminance values I1, I2 and I3 of the points-corresponding-to-pixels E1, E2 and E3 are expressed by a following formulas (3).

[Formulas 3]

$$I_1 = hI_q \cos \beta_1 / |\vec{r}_1|^2$$

$$I_2 = hI_q \cos \beta_2 / |\vec{r}_2|^2$$

$$I_3 = hI_q \cos \beta_3 / |\vec{r}_3|^2 \quad (3)$$

Here, h denotes the diffuse reflectance of the surface of the target body; Iq denotes the light intensity of the light source Q; β denotes the angle formed by the normal vector n of the surface of the target body at a point P and a vector r from the light source Q to the point P. The point P in FIG. 8A represents the points-corresponding-to-pixels E1, E2 and E3 in FIG. 7 (therefore, the vector r represents the vectors r1, r2 and r3 in FIG. 7).

Next, conditions (a) and (b) described below are set, and the three-dimensional positions of the target body corresponding to the pixels of the picked-up image are calculated on the assumption that the conditions (a) and (b) are satisfied.

An approximation formula (4) shown below is obtained if the conditions (a) and (b) are satisfied. The condition (a): distance between observation point O and light source Q<distance between observation point O and three-dimensional positions of points-corresponding-to-pixels E1, E2 and E3, that is, |d|<<|rm| (or |d|<<|r|; wherein m=1 to 3); and the condition (b): the three-dimensional positions of the points-corresponding-to-pixels E1, E2 and E3 are close to one another.

[Formula 4]
$$k_1:k_2:k_3 \approx 1/\sqrt{I_1} : 1/\sqrt{I_2} : 1/\sqrt{I_3} \qquad (4)$$

As shown in FIG. 8B, the above condition (a) is satisfied if the absolute value of r is larger than the absolute value of d. In the case of picking up an image of a tubular internal surface such as that of an esophagus, the condition (b) is considered to be satisfied in almost all cases. FIG. 8B shows the distal end surface portion of the distal end portion 14 magnified.

On the distal end surface, there is provided an illumination window 13a to which the distal end surface of the light guide 13 (or an illumination lens) is attached, and an illumination light is emitted from the illumination window 13a. That is, the illumination window 13a of the distal end surface or the like of the light guide 13 corresponds to the light source Q in FIGS. 7 and 8A. The observation point O adjacent to the illumination window 13a is an observation window (an image pickup window) at which the objective lens 15 of the image pickup means (the image pickup apparatus 17) is arranged.

From the above formula (4), the ratio of k1, k2 and k3 are determined, and the normal vector n is determined. Around a point-corresponding-to-pixel on the surface of the target body corresponding to each pixel in the image, there are multiple adjacent points-corresponding-to-pixels. Therefore, as shown in FIG. 9, normal vectors n1 to n4 are determined for planes formed by three points among points Pb to Pe around one point-corresponding-to-pixel Pa, respectively. It is possible to calculate a mean vector of the multiple normal vectors n1 to n4 and set the mean vector as the normal vector of the point-corresponding-to-pixel.

Assuming that the surface of the target body causes diffuse reflection as shown in FIG. 8A and, furthermore, rewriting the angle β, a luminance value I(x, y) of each point-corresponding-to-pixel P(x, y) can be expressed by the formula (5) as below:

[Formula 5]
$$I_{(x,y)} = hI_q \cos\beta / r^2 = hI_q \vec{n}_{(x,y)} \cdot \vec{r}_{(x,y)} / |\vec{r}_{(x,y)}|^3 \qquad (5)$$

Here, h denotes the diffuse reflectance of the target surface; Iq denotes the light intensity of the light source Q, β denotes the angle formed by the normal vector n(x, y) of the surface of the target body at the point P and the light source direction r(x, y).

The light source direction r(x, y) at the point P can be expressed by a formula (6) as shown below.

[Formula 6]
$$\vec{r}_{(x,y)} = k_{(x,y)} \vec{m}_{(x,y)} - \vec{d} \qquad (6)$$

Here, as shown in FIG. 8B, d denotes the vector from the observation point O of the objective lens 15 to the light source Q; m(x, y) denotes the unit vector from the observation point O to the position P on the target subject (concretely a tubular surface of a large intestine); and k(x, y) denotes a distance OP.

Since the vector m(x, y) passes through a position (x, y) on an image on an image-pickup surface 42 (of the CCD 16) as shown in FIG. 10, the vector m(x, y) is as shown by a formula (7) below:

[Formula 7]
$$\vec{m}_{(x,y)} = \begin{pmatrix} x/\sqrt{x^2+y^2+f^2} \\ y/\sqrt{x^2+y^2+f^2} \\ f/\sqrt{x^2+y^2+f^2} \end{pmatrix} \qquad (7)$$

Here, f denotes a focal distance of the image pickup apparatus 17. Therefore, the luminance value I(x, y) of each pixel on the image can be expressed by a formula (8) as shown below:

[Formula 8]
$$I_{(x,y)} = hI_q \vec{n}_{(x,y)} \cdot (k_{(x,y)} \vec{m}_{(x,y)} - \vec{d}) / |k_{(x,y)} \vec{m}_{(x,y)} - \vec{d}|^3 \qquad (8)$$

All except k(x, y) are known in the above formula (8). Therefore, k(x, y) is calculated from the formula (8), and a three-dimensional position (X, Y, Z) corresponding to each pixel (x, y) on the image is calculated as shown by a formula (9) below:

[Formula 9]
$$\begin{pmatrix} X \\ Y \\ Z \end{pmatrix} = k_{(x,y)} \vec{m}_{(x,y)} = k_{(x,y)} \begin{pmatrix} x/\sqrt{x^2+y^2+f^2} \\ y/\sqrt{x^2+y^2+f^2} \\ f/\sqrt{x^2+y^2+f^2} \end{pmatrix} \qquad (9)$$

In this way, a surface model as a three-dimensional shape as shown in FIG. 11 is generated. Each position P on the internal surface of the three-dimensional surface model shown in FIG. 11 passes through the position (x, y) on the two-dimensional image of the image pickup surface 42 as shown in FIG. 10, and it is generated with the use of the data of each position (x, y) on the image. Therefore, the number of data points in the two-dimensional image used to generate (constitute) the portion included in the voxel B which is a small area at each position P decreases as the distance from the observation point O or the image pickup surface 42 increases.

The number of data points changes depending on the angle formed by the plane at each position P and the image pickup surface 42, and the like. It is conceivable that the number of data points in this case is closely related to the amount of information indicating the reliability of the three-dimensional position of the voxel B.

Therefore, in the present embodiment, in the case of calculating, for a voxel B set on the internal surface of a generated three-dimensional shape, a voxel reliability indicating the reliability of the voxel B, the number of data points is considered as described below. By doing so, it is possible to provide, in the case of performing detection or judgment of a lesion candidate with the use of the generated three-dimensional surface model, information about the reliability of the detection result or the judgment result and enable confirmation or improvement of the reliability of the detection result and the like.

As for the internal surface of the three-dimensional surface model shown in FIG. 11, when there are convex portions on the internal surface (denoted by G1 and G2 in FIG. 11), internal surface portions which are positioned behind the convex portions when seen from the side of the observation position O are hidden. The portions behind the convex portions are in a state of being hidden, that is, a state of so-called occlusion. Occlusion portions H1 and H2 are portions which lack data.

Then, the CPU 22 scans the data of the three-dimensional shape generated by step S3 in FIG. 6, and performs interpolation processing of the occlusion portions H1 and H2 and the like as shown in step S4. In this case, for the data points at a surface position generated by the interpolation processing, a coefficient w, which is smaller than 1, is stored in association with the surface data.

In this way, interpolation is performed for the portions which lack data, and a surface model as shown in FIG. 4 is generated. The data of the surface model (referred to as surface model data) is stored, for example, in the information storage section 25 in FIG. 1.

Then, the CPU 22 performs voxel reliability map generation processing shown in FIG. 12. When the processing starts, the CPU 22 performs initial setting (sets a position parameter s described below for an initial value sin i) at step S11. After that, at next step S12, with the use of the surface model data stored in a surface model data storage section 25a of the information storage section 25, the CPU 22 sets each voxel Bxyz (abbreviated as Bs) on the surface model and calculates a distance Ls between the center position of the voxel Bs and the observation position (that is, the observation point O) as shown in FIG. 13.

The distance Ls can be calculated as an objective numerical value by applying an average diameter value of the large intestine 31 the image of which has been actually picked up, to the diameter of a tabular shape portion of an endoscopic image picked up. Though the distance Ls between the central position of the voxel Bs and the observation position (or the observation point O) is calculated here, the distance (denoted by Lsq) between the central position of the voxel Bs and the light source Q (illumination window) may be calculated with the use of the value of the vector d of OQ as shown in FIG. 8B. It may be assumed that the size of the vector d is smaller in comparison with the distance Lsq and that Ls≈Lsq is satisfied. The distance may be regarded as the distance from the distal end surface of the endoscope to the central position of the voxel Bs.

In the case where the observation position is regarded as the observation point and set as the origin (0, 0, 0) of surface model generation, the voxel Bs is such a small area the one side of which is 1 that $Vx \leq X < Vx+1$, $Vy \leq Y < Vy+1$ and $Vz \leq Z < Vz+1$ are satisfied when the coordinate position of the center of the voxel Bs is denoted by $(Vx+\frac{1}{2}, Vy+\frac{1}{2}, Vz+\frac{1}{2})$. For the small area, following processing is performed (the subscript s simply denotes the position of such a voxel Bs on the surface model that the three-dimensional coordinate position $(Vx+\frac{1}{2}, Vy+\frac{1}{2}, Vz+\frac{1}{2})$ is different).

Then, at next step S13, the CPU 22 acquires, for each voxel Bs, the number of constituent data points (shortened as the number of data points) Ns which constitute the surface model data. In this case, as for the number of data points Nsh configured by interpolation processing, the number of data points Ns is calculated by multiplying the number of data points Nsh by the coefficient w which is smaller than 1.

At next step S14, the CPU 22 calculates a voxel reliability ρs of the voxel Bs. For example, the ρs is:

$$\rho s = (1/Ls)(Ns/1 \cdot 1 \cdot 1)\alpha \quad (10)$$

wherein α denotes a normalizing factor, and the number of data points Ns is the sum of the number of true data points Nsi, for which interpolation processing has not been used, and the number of data points Nsh generated by interpolation processing multiplied by the factor w (smaller than 1).

That is, a formula (11) is obtained:

$$Ns = Nsi + w \cdot Nsh \quad (11)$$

Then, the CPU 22 stores the calculated value of the voxel reliability ρs in a voxel reliability map storage section 25b provided in the information storage section 25 in association with the position data of the voxel Bs.

The value of the voxel reliability ρs is smaller as the distance Ls from the light source Q or the observation position (observation window) is larger, and the value is smaller as the number of data points in the voxel Bs is smaller. Therefore, the value is evaluation means for appropriately evaluating the reliability of the point (small area) of each portion on the generated surface model.

Then, at next step S15, the CPU 22 performs condition judgment on whether setting of the voxel Bs has been performed for all the surface model data (in other words, the CPU 22 performs condition judgment on whether the final parameter value sfin has been reached). If the condition is not satisfied, the CPU 22 changes the value of the parameter s by one and returns to step S12, as shown by step S16.

When the processing for calculating the voxel reliability ρs has been ended for all the surface model data in this way, a voxel reliability map in which the reliability of each point (a voxel as a small area) on the surface model is calculated is generated in the voxel reliability map storage section 25b.

There are mainly two methods for utilizing the voxel reliability map generated in this way.

In one of the two methods, the surface shape of the generated surface model is, for example, pseudo-colorized by the calculated voxel reliability ρs of the voxel reliability map and displayed.

For example, an ordinary surface model display image and a surface model pseudo-colorized by the voxel reliability ρs are displayed together. In this case, the models may be displayed in the same size.

As a variation of the display described above, it is also possible that, when a user such as an operator specifies a region or an area to be noticed as a lesion candidate on the surface model with instruction means such as a mouse not shown, the CPU 22 reads a voxel reliability corresponding to the specified area portion from the voxel reliability map and displays the voxel reliability.

Thus, the reliability of each area on a surface model can be presented. Therefore, when an operator performs lesion diagnosis or the like with the use of a surface model, information about the reliability of the surface model can be provided, and it is possible to enable confirmation of reliability and to improve reliability.

Next, in the second utilization method, when detection of a lesion candidate or lesion judgment of a lesion candidate is performed with the use of a surface model by image processing, information about the reliability of the detection result or the judgment result is provided.

As an example of the case, a case of extracting a polyp candidate in a large intestine and further performing detection (judgment) with the use of a voxel reliability map will be described below.

FIG. 14 is a block diagram showing a polyp candidate extraction/judgment processing program in the present embodiment and data used by the program.

When the processing starts, the CPU 22 reads the polyp candidate extraction/judgment processing program stored in the processing program storage section 23 in FIG. 1, and starts polyp candidate judgment function 22c shown in FIG. 5 in accordance with the program.

As shown in FIG. 14, at first step S21, the CPU 22 takes in, for example, an R signal component of an original image 51 stored in the image storage section 24 (see FIG. 1) in the image processing apparatus 3 and performs edge extraction processing. In this case, an edge image 52 is generated, for example, by applying a band-pass filter to the R signal component. The edge extraction method using a band-pass filter is a well-known technique. Instead of the R signal component, the luminance component of the original image 51 may be used to generate the edge image 52.

At next step S22, the CPU 22 performs binarization processing of the edge image 52. Then, a binarized image 53 is generated by the binarization processing. In the binarization processing in the present embodiment, each pixel of the binarized image 53 is determined as 0 or 1 on the basis of a result of size comparison between the pixel value of each pixel of the edge image 52 and a specified or predetermined threshold.

At next step S23, the CPU 22 applies a well-known line thinning method to the binarized image 53 and generates a line-thinned image 54.

At next step S24, the CPU 22 performs extraction processing for extracting candidate points having a predetermined feature value of a curved edge shape and the like, such as a polyp candidate as a protrusion lesion, from the line-thinned image 54 as a two-dimensional image. In this case, the CPU 22 performs processing for extracting two end points of an edge to be noticed and the middle point between the two end points, and the middle point on the line connecting the two end points of the edge and storing them as lesion candidate point information 55 of the two-dimensional image.

The processing will be described with reference to FIGS. 15A to 15D. FIG. 15A shows the line-thinned image 54. The CPU 22 acquires an edge portion for which judgment processing is to be performed, from the line-thinned image 54. Next, as shown in FIG. 15B, the CPU 22 extracts two end points t1 and t2 of the edge.

Next, the CPU 22 calculates the number of pixels of the edge as a line segment length D1 (not shown), and further calculates a middle point t (FIG. 15C) corresponding to ½× D1.

Next, the CPU 22 extracts a line connecting t1 and t2, calculates the line segment length D2 (not shown) of the line and, after that, calculates a middle point p (FIG. 15D) corresponding to ½×D2.

Next, the CPU 22 stores the information about the calculated candidate points of the two-dimensional image (the two end points t1 and t2 of the edge, the middle point t of the two points t1 and t2, and the middle point p on the line connecting the two end points t1 and t2 of the edge).

Next, at step S25 shown in FIG. 14, the CPU 22 performs processing for extracting data of candidate points on the three-dimensional image (surface model) corresponding to the candidate points on the two-dimensional image.

That is, the CPU 22 acquires the coordinates of the candidate points on the two-dimensional image (the two end points t1 and t2 of the edge, the middle point t of the two points t1 and t2, and the middle point p on the line connecting the two end points t1 and t2 of the edge) on the three-dimensional surface model and stores the candidate point coordinate information (three-dimensional) 56.

Then, at next step S26, the CPU 22 performs judgment of a possibility of a polyp candidate as a protrusion lesion, that is, polyp candidate judgment processing with the use of the candidate point coordinate information 56 (by image processing).

The polyp candidate judgment processing is shown in FIG. 16. In the description below, a case where the line connecting the two points t1 and t2 on the two-dimensional image is in parallel to an x axis will be described.

At first step S31, the CPU 22 acquires the information about the coordinates of the candidate points on the three-dimensional surface model described above. At next step S32, the CPU 22 calculates a y coordinate py of the middle point p on the line connecting the two end points t1 and t2 of the edge and calculates an xz plane including the py and the two points t1 and t2. The middle point p is approximated to the same as or close to the value of the y coordinate on the line connecting the two end points t1 and t2 of the edge.

The vicinity of the candidate points 56 on the surface model in this case is shown in FIG. 17. This portion corresponds, for example, to the portion denoted by reference numeral G1 in FIG. 13.

At next step S33, the CPU 22 draws a perpendicular on the xz plane determined by the points t1, t2 and py, from the point t and calculates a height h of the perpendicular. Then, as shown in FIG. 17, the CPU 22 judges which of the height h and a predetermined threshold Tth is larger at next step S34. In the case of h>Tth, the CPU 22 proceeds to step S35. Otherwise, that is, in the case of h≦Tth, the CPU 22 judges that the edge portion is not a polyp candidate and ends the processing.

The point t at step S33 is a point (position) set at the middle point between the points t1 and t2 on the two-dimensional image. It is possible to determine the values of perpendiculars in the vicinity of the point t on the three-dimensional surface model and calculate a maximum value as the height h.

At step S35, the CPU 22 judges the edge portion obtained by the processing of step S24 in FIG. 14 as a polyp candidate.

In the case where the two points t1 and t2 described above are not in parallel to the x axis, a height (denoted by hy) from the point t to a yz plane is calculated, and the root of the two squared values is calculated. Then, the calculated value and the threshold Tth are compared to determine which is larger.

At next step S36, the CPU 22 extracts voxel reliabilities (of voxels) corresponding to, for example, the edge portion (the points t1, t2, t, p (py) and the like) used for the judgment of the polyp candidate described above, from the voxel reliability map, and calculates an average value ρa of the voxel reliabilities.

Then, at next step S37, the CPU 22 presents the portion which has been judged to be a polyp candidate, for example, shown in a color different from the color of other portions so as to be recognized by a user, on the display monitor 4 or the like, and presents the average value ρa as information indicating the reliability of the judgment.

Then, if there is another edge in the line-thinned image, similar processing is performed. Then, after similar processing is performed for all edges, the polyp candidate judgment processing is ended.

Thus, for example, when a large intestine polyp candidate as a protrusion lesion in a large intestine examination is presented by the image processing apparatus 3, information indicating the reliability of the result of judgment is simultaneously presented, for example, as the average value ρa described above.

Since the average value ρa is calculated with the use of the voxel reliability ρs of the portion used to make a judgment of a polyp candidate, it is one of evaluation means for appropriately evaluating the result of the polyp candidate judgment.

Therefore, an operator can quantitatively judge the reliability of a large intestine polyp candidate concerned. Thus, since it becomes possible to quantitatively judge the reliability of the large intestine polyp candidate judgment function, the average value pa is data or information effective in assisting lesion judgment by an operator.

In the description above, for example, in the case of calculating the voxel reliability ρs, information about the luminance values on the two-dimensional image may be included.

For example, it is possible to exclude values (luminance values) corresponding to dark portions and halation, and set a larger weighting coefficient for a larger luminance value in that case to reflect the luminance value on the voxel reliability. That is, the reliability of a portion with a large luminance value is higher than the reliability of a portion with a small luminance value because the portion with a large luminance value is less affected by noises and the like than the portion with a small luminance value. Therefore, the luminance value information may be reflected on the voxel reliability.

The case of calculating the (voxel reliability) map for all the portions on a surface model is not restrictive. As a variation of the embodiment described above, the voxel reliability map may be calculated with the use of only representative points. Only the voxel reliability of a portion to be used for lesion detection (judgment) may be calculated.

In the above example, description has been made on the case of judging a candidate for a polyp as a protrusion lesion. However, the present embodiment can be similarly applied to a candidate for a depression lesion also. In this case, a depth h' is calculated instead of the height h. Then, if the depth h' is larger than a threshold Tth', the target is judged to be a depression lesion candidate, and otherwise, the target is judged not to be a candidate.

In the embodiment described above, for example, as the polyp candidate judgment processing, information about the height threshold Tth is used to make a judgment. In addition thereto, judgment (detection) may be performed with the use of shape index and curvedness which are feature values indicating a curved surface shape.

In this case also, candidate judgment is not limited to the case of a protrusion lesion but may be performed in the case of a depression lesion. Furthermore, judgment using only the height threshold Tth is not restrictive. Judgment (detection) may be performed with the use of a threshold indicating the size of the area, for example, a threshold of curvedness.

A variation made by combination or the like of the contents of the above embodiment without changing the essentials thereof also belongs to the present invention.

As described above, according to the present invention, in the case of generating a three-dimensional surface model from a medical image such as a two-dimensional endoscopic image, by image processing, and detecting a candidate for a lesion such as a polyp or judging a possibility of a lesion with the use of the data of the generated surface model, information about the reliability of a result of the detection and the like is presented in consideration of the reliability of data of each part of the surface model used for the result of the detection or the result of the judgment. Thus, the present invention has an industrial applicability of enabling an operator to make a diagnosis more appropriately.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A medical image processing apparatus comprising:
a surface model generation section for performing processing for generating a three-dimensional surface model from a two-dimensional medical image;
an area reliability calculation section for dividing the surface model into multiple areas and calculating the area reliability of data in each of the multiple areas; and
a candidate detection section for detecting a candidate having a predetermined feature value from the two-dimensional medical image or the surface model,
wherein, for the candidate detected by the candidate detection section, the reliability of the candidate detection result is calculated with the use of the area reliability of each of the areas in the surface model utilized for the candidate detection.

2. The medical image processing apparatus according to claim 1, wherein:
the two-dimensional medical image is an endoscopic image picked up by an endoscope; and
the area reliability calculation section calculates the area reliability with the use of information about the distance between each of the areas and an illumination window or an image pickup window of the endoscope and information about the number of constituent data points constituting the surface model included within the area.

3. The medical image processing apparatus according to claim 2, wherein the area reliability calculation section calculates the area reliability of a value that is approximately inverse proportion to a distance between the each area and the illumination window or the image pickup window, and is approximately proportion to a number of data points constituting the surface model included in the area.

4. The medical image processing apparatus according to claim 1, wherein the candidate detection section detects a candidate region having a feature value of protrusion or depression, as the candidate having the predetermined feature value.

5. The medical image processing apparatus according to claim 4, the candidate detection section extracts a portion having a feature value of protrusion or depression as a candidate, and, if the height or the depth of the extracted portion is equal to or above a threshold, detects or judges the extracted portion to be a protrusion lesion or a depression lesion.

6. The medical image processing apparatus according to claim 5, wherein the candidate detection section detects or judges a candidate region having a feature value of protrusion or depression, as the candidate having the predetermined feature value.

7. The medical image processing apparatus according to claim 1, wherein the surface model generation section performs generation processing of a three-dimensional surface model of the subject with the use of information about a single two-dimensional medical image of the subject irradiated with illumination light of a light source, the image being picked up by an image-pickup device, information about a position of the light source when the medical image is picked up, and information about a position of an observation point of an objective lens that forms an image on the image-pickup device when picking up the medical image.

8. The medical image processing apparatus according to claim 7, wherein the surface model generation section generates the surface model of the subject with the use of a unit vector m which is in a direction from the observation point to a three-dimensional position on the subject corresponding to a position of a pixel on the single two-dimensional medical image and which is in a direction passing the position of the pixel, and information about a luminance value I at a three-dimensional position of the subject including an assumption of diffuse reflection that a surface of the subject uniformly reflects light in all directions.

9. A medical image processing method comprising:
a surface model generation step of performing processing for generating a three-dimensional surface model from a two-dimensional medical image;
an area reliability calculation step of dividing the surface model into multiple areas and calculating, by a processor device, the area reliability of data in each of the multiple areas; and
a candidate detection step of detecting by the processor device a candidate having a predetermined feature value, from the two-dimensional medical image or the surface model, wherein, for the candidate detected by the candidate detection step, the reliability of the candidate detection result is calculated by the processor device with the use of the area reliability of each of the areas in the surface model utilized for the candidate detection.

10. The medical image processing method according to claim 9, wherein:

the two-dimensional medical image is an endoscopic image picked up by an endoscope; and the area reliability calculation step calculates, by the processor device, the area reliability with the use of information about the distance between each of the areas and an illumination window or an image pickup window of the endoscope and information about the number of constituent data points utilized for configuration of the surface model included within the area.

11. The medical image processing method according to claim 10, wherein the area reliability calculation step calculates the area reliability of a value that is approximately inverse proportion to a distance between the each area and the illumination window or the image pickup window, and is approximately proportion to a number of data points constituting the surface model included in the area.

12. The medical image processing method according to claim 9, wherein the surface model generation step performs, by the processor device, generation processing of a three-dimensional surface model of the subject with the use of information about a single two-dimensional medical image of the subject irradiated with illumination light of a light source, the image being picked up by an image-pickup device, information about a position of the light source when the medical image is picked up, and information about a position of an observation point of an objective lens that forms an image on the image-pickup device when picking up the medical image.

13. The medical image processing method according to claim 12, wherein the surface model generation step generates the surface model of the subject with the use of a unit vector m which is in a direction from the observation point to a three-dimensional position on the subject corresponding to a position of a pixel on the single two-dimensional medical image and which is in a direction passing the position of the pixel, and information about a luminance value I at a three-dimensional position of the subject including an assumption of diffuse reflection that a surface of the subject uniformly reflects light in all directions.

14. The medical image processing method according to claim 9, wherein the candidate detection step extracts a portion having a feature value of protrusion or depression as a candidate, and, if the height or the depth of the extracted portion is equal to or above a threshold, detects or judges the extracted portion to be a protrusion lesion or a depression lesion.

* * * * *